US011067551B2

(12) United States Patent
Vandroux et al.

(10) Patent No.: US 11,067,551 B2
(45) Date of Patent: Jul. 20, 2021

(54) DEVICE FOR MEASURING THE AMOUNT OF OXYGEN PRESENT IN A GAS, AND AIR-SEPARATION MODULE COMPRISING SUCH A MEASUREMENT DEVICE

(71) Applicants: ZODIAC AEROTECHNICS, Roche la Moliere (FR); L'Air Liquide Societe Anonyme Pour L'Etude et L'Exploitation Des Procedes Georges Claude, Paris (FR)

(72) Inventors: Olivier Vandroux, Grenoble (FR); Nelly Giroud, Saint-Etienne (FR); Norbert Ponsinet, Plaisir (FR); Jorge Gaspar, Gagny (FR); Gilles Delaitre, Beauchamp (FR); Jean-Michel Cazenave, Seyssins (FR); Philippe Boggetto, Sassenage (FR)

(73) Assignees: ZODIAC AEROTECHNICS, Roche la Moliere (FR); L'Air Liquide Societe Anonyme Pour L'Etude et L'Exploitation Des Procedes Georges Claude, Paris (FR)

( * ) Notice: Subject to any disclaimer, the term of this patent is extended or adjusted under 35 U.S.C. 154(b) by 81 days.

(21) Appl. No.: 16/475,905

(22) PCT Filed: Jan. 5, 2018

(86) PCT No.: PCT/FR2018/050025
§ 371 (c)(1),
(2) Date: Jul. 3, 2019

(87) PCT Pub. No.: WO2018/127667
PCT Pub. Date: Jul. 12, 2018

(65) Prior Publication Data
US 2019/0369074 A1    Dec. 5, 2019

(30) Foreign Application Priority Data

Jan. 9, 2017  (FR) ...................................... 1750185

(51) Int. Cl.
*G01N 33/00*     (2006.01)
*B64D 37/32*     (2006.01)
*G01N 27/417*    (2006.01)

(52) U.S. Cl.
CPC ..... *G01N 33/0006* (2013.01); *G01N 33/0073* (2013.01)

(58) Field of Classification Search
CPC .......... G01N 33/0006; G01N 33/0073; G01N 27/4175; B64D 37/32
See application file for complete search history.

(56) References Cited

U.S. PATENT DOCUMENTS 4,516,424 A * 5/1985 Rowland ............... A61M 16/10
73/1.06
7,040,319 B1 * 5/2006 Kelly .................... A61M 16/06
128/204.22

(Continued)

OTHER PUBLICATIONS

International Search Report issued in PCT Patent Application No. PCT/FR2018/050025 dated Jun. 29, 2018.

(Continued)

*Primary Examiner* — Peter J Macchiarolo
*Assistant Examiner* — Anthony W Megna Fuentes
(74) *Attorney, Agent, or Firm* — Marshall, Gerstein & Borun LLP

(57) ABSTRACT

The present disclosure relates to a device for measuring the amount of oxygen present in a gas to be analyze. The device includes at least one member for measuring the amount of oxygen, a first inlet in communication with the measuring member for the supply of gas to be analyzed, and an outlet for the discharge of said analyzed gas. The device also (Continued)

includes a second inlet intended to communicate with the measuring member, allowing said device to be supplied selectively with a calibration gas having a known amount of oxygen, such that the measurement of the amount of oxygen present in the calibration gas makes it possible to determine a potential drift of the measurement of said measuring member relative to the actual known amount of oxygen present in the calibration gas.

6 Claims, 2 Drawing Sheets

(56) References Cited

U.S. PATENT DOCUMENTS

| | | | |
|---|---|---|---|
| 7,385,692 B1 | 6/2008 | Nguyen | |
| 9,631,567 B2* | 4/2017 | Song | F02D 41/2474 |
| 2006/0275718 A1* | 12/2006 | Arnold | F23G 5/24 |
| | | | 431/13 |
| 2011/0263035 A1* | 10/2011 | Beeson | G01N 27/16 |
| | | | 436/138 |
| 2015/0219554 A1 | 8/2015 | Hedges et al. | |

OTHER PUBLICATIONS

Anonymous, "The Direct Insertion Type Zirconia Oxygen Analyzer Detector Type: ZFKE, rev. 1st edition," https://americas.fujielectric.com/files/prod_selector_v/Zirconia Oxygen Analyzer Detector (Flameproof) Model ZFKE (2011).

* cited by examiner

DEVICE FOR MEASURING THE AMOUNT OF OXYGEN PRESENT IN A GAS, AND AIR-SEPARATION MODULE COMPRISING SUCH A MEASUREMENT DEVICE

TECHNICAL FIELD

The present invention relates to a device for measuring the amount of oxygen present in a gas, as well as an air separation module comprising such a measuring device. "Amount of oxygen" in particular refers to the proportion or percentage of oxygen.

The invention is advantageously applicable to verify the percentage or partial pressure of oxygen contained in the gas generated, for example, by a system for producing inert gas on board an aircraft, such as an airplane.

Another advantageous application falls within the measurement of the percentage of oxygen present in a volume, such as a fuel tank, for example, to verify the flammability properties thereof.

PRIOR ART

In the aeronautics field, systems are known for inerting fuel tanks of an aircraft comprising air separation modules having permeable membranes, such as polymer membranes, passed through by an air flow. Due to the different permeabilities of the membranes to nitrogen and oxygen, the system splits the air flow so that an air flow with high nitrogen content and an air flow with high oxygen content are obtained.

The air fraction enriched with nitrogen is conveyed into the fuel tanks of the aircraft such that the oxygen concentration of the mixture of air and kerosene vapor present in this location is decreased to make said tank inert.

Alternatively, the air fraction enriched with oxygen may be reintroduced into the passenger cabin after having been treated using appropriate means.

In these applications, it is important to know precisely the amount of oxygen present in the gas discharged by said air separation module, especially regarding the gas intended to make a fuel tank inert.

To that end, it is known to use a measuring device implementing a measuring means provided with a zirconium probe to perform the necessary measurements in said gas to determine the amount of oxygen. The zirconium probe is in particular powered by a fixed voltage.

However, this type of measuring device is sensitive to environmental conditions, and the measurement that it provides can drift uncontrollably. Indeed, the measurements done by the zirconium probe are variable based upon environmental usage conditions of said probe, and in particular based upon the ambient temperature in which the measuring means is kept.

Furthermore, the measurement done by the probe drifts randomly over time, since it does not account for the aging of the zirconium-based sensitive element.

Another drawback lies in the management of the probe, which also does not account for the disparities related to its manufacturing process.

Lastly, in the considered application consisting of analyzing an inerting gas, the verifications of the precision of the measuring device, with the aim of making sure that the signal given off by the probe has not drifted, are done too infrequently, in particular only during maintenance operations. Furthermore, the described analyzer has a function making it possible to determine the origin of any malfunctions, thus making it possible to save time during maintenance operations.

DISCLOSURE OF THE INVENTION

One aim of the invention is therefore to resolve these drawbacks by proposing a device that makes it possible to measure the amount of oxygen present in a gas, reliably and precisely over time.

Another aim of the invention is in particular to provide such a measuring device that is not sensitive to the environmental conditions, so as to limit the drift of its measurement, or even to eliminate it.

Another aim of the invention is to provide such a measuring device that can be installed at the outlet of an air separation module of a system for inerting aircraft fuel tanks.

To that end, a device has been developed for measuring the amount of oxygen present in a gas to be analyzed according to the state of the art in that it comprises at least one member for measuring the amount of oxygen, a first inlet intended to communicate with the measuring member for the supply of gas to be analyzed, and an outlet for the discharge of said analyzed gas.

According to the invention, the device comprises a second inlet intended to communicate with the measuring member, allowing said device to be supplied selectively with a calibration gas having a known amount of oxygen, such that the measurement of the amount of oxygen present in the calibration gas makes it possible to determine a potential drift of the measurement of said measuring member relative to the actual known amount of oxygen present in the calibration gas.

Indeed, the calibration gas makes it possible to verify that the measurement given by the measuring device is not altered and indeed corresponds to the reality. For example, the calibration gas used can be the ambient air, the composition of which is known, at any point around the globe and up to an altitude of 15 kilometers, to be 20.9% oxygen. In this way, by comparing the value of the actual amount of oxygen present in the ambient air with the value of the measurement given by the device according to the invention, it is possible on the one hand to verify the potential drift of the measuring member, and on the other hand to calibrate said measuring member so that it provides an accurate measurement.

Advantageously, the measuring device according to the invention comprises a microcontroller governed by the measuring member to perform an automatic recalibration of the measuring member based on the determined drift. This operation can be done in real-time and at any moment, simply and quickly. Thus, it is not necessary to wait for maintenance operations to verify the drift of the measuring member and recalibrate it if necessary. The measuring device according to the invention therefore has an optimal measuring precision over the entire usage range.

According to one particular embodiment, the measuring device according to the invention comprises a selection module controlled by the microcontroller and able to place, as selected, the first or second inlet in communication with the measuring member to analyze either the gas coming from the first inlet or the calibration gas coming from the second inlet.

According to one specific embodiment, the selection module, preferably pneumatic, comprises a solenoid valve comprising two inlets, respectively connected to the first and second inlet of the measuring device, and an outlet in communication with the measuring member.

For example, the member for measuring the amount of oxygen comprises a zirconium probe able to measure the partial pressure of oxygen present in a gas, from which it is possible to deduce a amount of oxygen present in the gas.

Advantageously, the device comprises a temperature sensor arranged at the zirconium probe and governed by the microcontroller, such that the microcontroller is able to vary the supply voltage of the zirconium probe based on the measured temperature to keep the core of the probe at a constant temperature.

Advantageously, the device according to the invention comprises a pressure sensor arranged at the zirconium probe to measure the pressure at the measuring point. Said pressure sensor is governed by the microcontroller to allow said microcontroller to calculate the percentage of oxygen present in the gas from the partial pressure of oxygen.

The invention also seeks to provide an air separation module to generate inerting gas in a system for inerting at least one fuel tank of an aircraft. The module inwardly has at least one permeable membrane, and comprises an inlet for compressed air intended to pass through the membrane, an outlet for air enriched with oxygen, and an outlet for oxygen-depleted air called inerting gas. According to the invention, the air separation module comprises a measuring device according to the aforementioned features, the first inlet of which is connected to the outlet for oxygen-depleted air of the air separation module, and the second inlet of which is connected or intended to be connected to a calibration gas source.

BRIEF DESCRIPTION OF THE FIGURES

Other advantages and characteristics will better emerge from the following description of the invention, provided by way of a non-limiting example, of a measurement device, based upon the appended drawings, wherein.

DETAILED DESCRIPTION OF THE INVENTION

Figure 1:
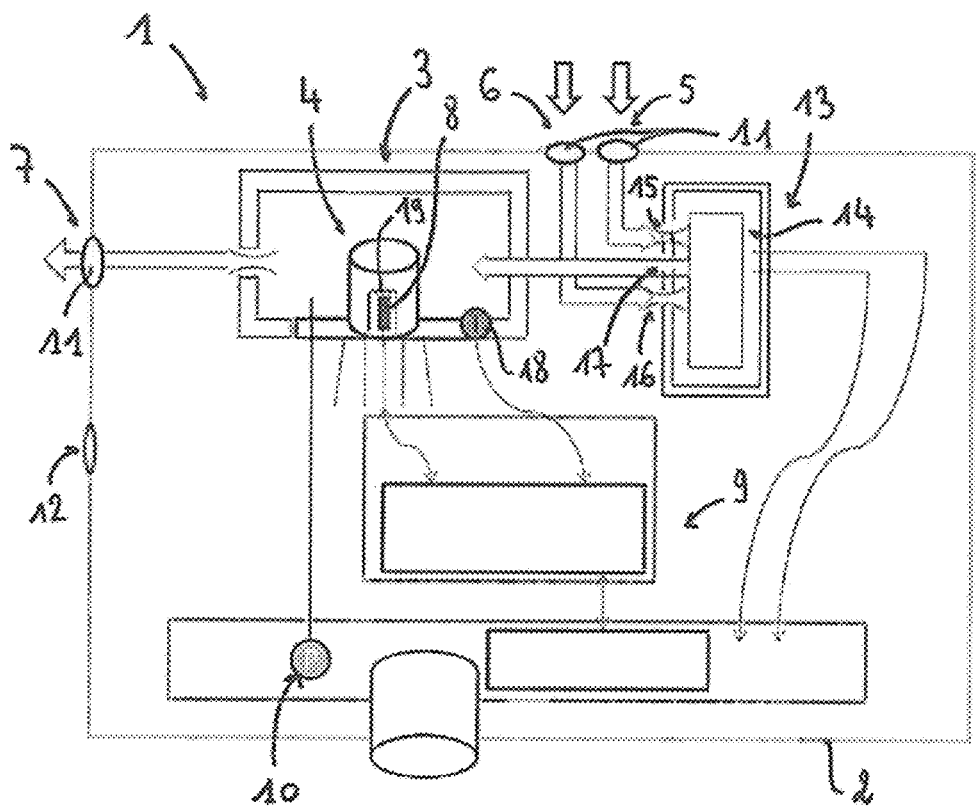
FIG. 1 is a detailed schematic view showing the operating diagram of the measuring device according to the invention.

In reference to FIG. 1, the invention relates to a device (1) for measuring the amount of oxygen present in a gas, and is advantageously applicable to measuring the amount of oxygen present in a gas discharged by an air separation module of an inerting system of an aircraft.

The measuring device (1) according to the invention for example comprises a casing (2) containing at least one member (3) for measuring the amount of oxygen for example comprising a zirconium probe (4). The casing (2) comprises a first inlet (5) intended to communicate with said probe (4) to supply gas to be analyzed, a second inlet (6) intended to communicate selectively with the probe (4) to supply it with a calibration gas, such as ambient air, having a known amount of oxygen, and an outlet (7) for the discharge of said analyzed gas.

To that end, the measuring member (3) comprises an inlet (3a) intended to be supplied with gas and a discharge outlet (3b), connected to the outlet (7) of the casing (2). In a known manner, the probe (4) comprises a detection cell (8) made from stabilized zirconium and implements electrodes for measuring the partial pressure of oxygen present in the gas. The zirconium probe (4) is well known from the state of the art, for example of type KGZ10, and is supplied by a microcontroller (9) with a direct voltage of about 4.5 V. To deduce the percentage of oxygen present in the gas, the device (1) according to the invention comprises a pressure sensor (10) arranged at the zirconium probe (4) to measure the pressure at the measuring point, and governed by the microcontroller (9) to make it possible to calculate the percentage of oxygen from the partial pressure of oxygen.

Figure 4:
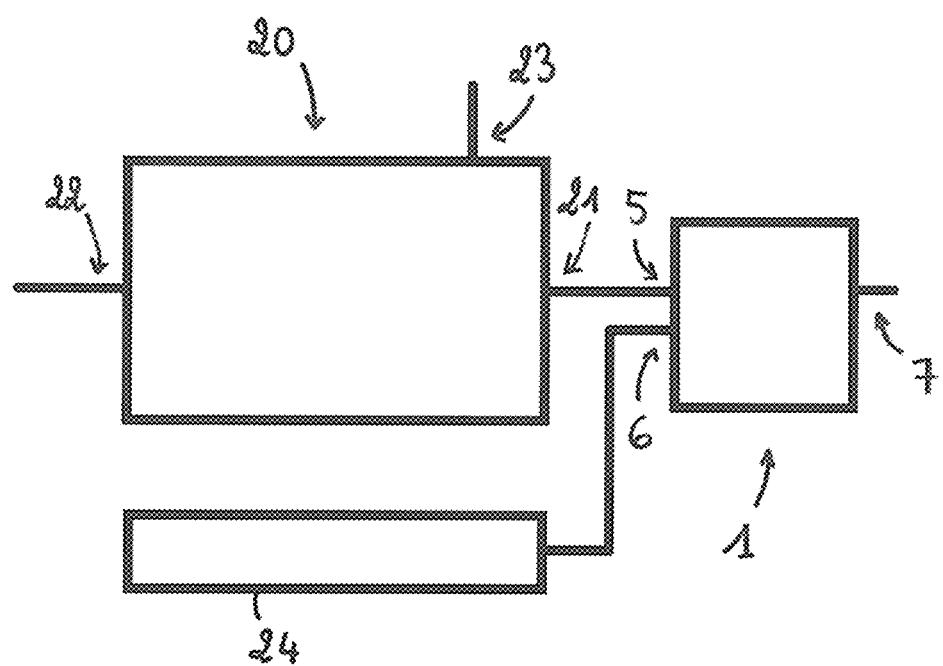
FIG. 4 is a schematic illustration of an air separation module according to the invention, comprising a device for measuring the amount of oxygen.

In practice, in reference to FIG. 4, and in the considered advantageous application, the measuring device (1) is connected, by means of the first inlet (5), to an inerting gas outlet (21) of an air separation module (20) intended, for example, to supply oxygen-depleted gas to a fuel tank to make it inert. More specifically, the air separation module (20) inwardly has at least one permeable membrane, and comprises an inlet (22) for compressed air intended to pass through the membrane, an outlet (23) for air enriched with oxygen, and the outlet (21) for oxygen-depleted air called inerting gas. The oxygen-depleted gas flow passes through the device (1) by passing through the inlet (5), communicates with the zirconium probe (4) for the measurement as such and by means of the inlet (3a) of the measuring member (3), and is next discharged through the outlet of the measuring member (3b) and through the outlet (7) of the device (1). The measurement of the amount of oxygen present in this gas is analyzed continuously and in real-time. In this application, the inlets (5, 6) and the outlet (7) of the measuring device (1) comprise filters and elements for stopping the progression of the flames (11). The device (1) also comprises a drainage orifice (12) making it possible to maintain a constant pressure inside the measuring device (1) and not to distort the measurement.

In practice, when it is necessary to verify the drift of the measurement given by the measuring device (1), and in particular to switch to the second inlet (6) connected to a calibration gas source (24) such as ambient air, the device (1) comprises a selection module, preferably pneumatic, (13) comprising a solenoid valve (14) comprising two inlets (15, 16), respectively connected to the first (5) and the second (6) inlet of the device (1), and an outlet (17) in communication with the zirconium probe (4).

Figure 2:
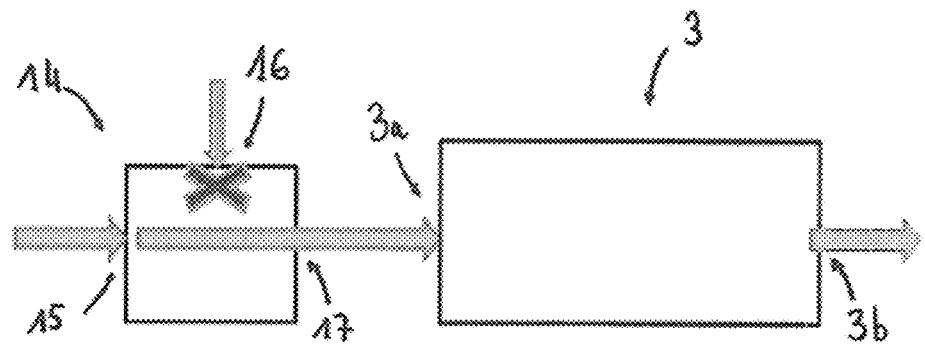
FIG. 2 is a schematic illustration showing the connection between the pneumatic selection module and the measuring member of the measuring device according to the invention, for measuring the amount of oxygen present in a gas for example coming from an air separation module.
Figure 3:
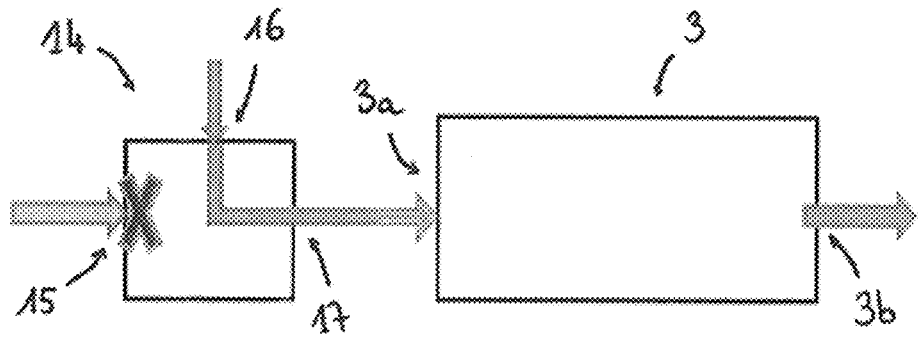
FIG. 3 is a schematic illustration similar to that of FIG. 2, for measuring the amount of oxygen present in a calibration gas, such as ambient air, for example.

In reference to FIGS. 2 and 3, the solenoid valve (14) is controlled by the microcontroller (9) to close off the first inlet (15) or the second inlet (16) of the solenoid valve (14), and to open the other to place the second inlet (6) or the first inlet (5) of the device (1) in communication with the zirconium probe (4).

The microcontroller (9) is therefore able to place the second inlet (6) of the measuring device (1) in communication with the probe (4) to perform periodic measurements of the amount of oxygen present in the calibration gas to make it possible to determine a potential drift of the probe (4) relative to the known actual amount of oxygen present in the calibration gas. Indeed, compared to the measurement obtained with the known actual quantity, namely for the ambient air 20.9% oxygen at any point around the globe and up to 15 km in altitude, the microcontroller (9) determines a potential drift of the measurement by the zirconium probe (4).

The microcontroller (9) is governed by the zirconium probe (4) to make it possible to perform an automatic recalibration of said probe (4) based on the determined drift. The microcontroller (9) for example applies a weight to the value measured by the zirconium probe (4) to readjust said measurement to the known actual value. The probe (4) is therefore recalibrated automatically, in real time and without needing a maintenance operation.

To optimize the measuring precision, the device (1) comprises a temperature sensor (18) arranged at the zirconium probe (4) and governed by the microcontroller (9), such that the microcontroller (9) is able to vary the supply voltage of the zirconium probe (4) based on the measured temperature, in particular to keep the core of the probe at a constant temperature. To that end, a resistance (19) makes it possible to heat the probe if necessary.

Thus, the measuring device (1) according to the invention makes it possible on the one hand to vary the supply voltage as a function of the ambient temperature and individual characteristics of the probe (4). This management results in keeping the core of the probe at a constant temperature in order to improve the precision of the measurement and not to be sensitive to environmental conditions and, on the other hand, to recalibrate the measurement if necessary during operation.

The measurement supplies a partial pressure of oxygen, which is used as such for OBOGS applications, according to the acronym "On-Board Oxygen Generating", which in particular relates to the implementation of autonomous breathing oxygen generation systems, from a withdrawal of engine air, but which is converted into an oxygen percentage via the absolute pressure sensor (10) placed near the probe (4), or for OBIGGS applications, according to the acronym "On-Board Inert Gas Generation Systems", which relate to the implementation of inert gas generating systems for inerting fuel tanks, for example.

All of the command and control logics are made from the microcontroller (9) integrated into the device (1) according to the invention. This microcontroller (9) is also used to generate alarm or proper operation signals of the various components of the measuring device (1).

The microcontroller (9) is associated with software that takes on correction curves characterizing at least a dozen zirconium probes (4) for example, tested under variable environmental conditions to determine the average response of said probes as a function of different ambient temperature cycles, ambient pressures, supply pressures, and oxygen content levels. These curves are integrated into the device (1) and make it possible to correct the drift of the device (1) if applicable.

The software also incorporates data relative to aging tests of the probe to determine its natural drift and make it possible to incorporate a self-verification and self-calibration function. The software in particular comprises calibration and adaptation laws of the control of the probe.

The microcontroller (9) also makes it possible to control the solenoid valve (14) for example to recover, at regular intervals, measurements of the amount of oxygen present in the calibration gas and produces, from said measurements, a graph of the drift of the zirconium probe (4) as a function of time.

It thus emerges from the preceding that the measuring device (1) according to the invention makes it possible to measure the amount of oxygen present in a gas, reliably and precisely, while not being sensitive to the environmental conditions, so as to limit the drift of its measurement, or even to eliminate it, and while allowing an automatic and real-time recalibration of the measurement, thereby limiting maintenance operations.

The invention claimed is:

1. A device for measuring the amount of oxygen present in a gas to be analyzed, said device comprising at least one member for measuring the amount of oxygen, a first inlet intended to communicate with the measuring member for the supply of gas to be analyzed, and an outlet for the discharge of said analyzed gas, the device comprises a second inlet intended to communicate with the measuring member, allowing said device to be supplied selectively with a calibration gas having a known amount of oxygen, such that a measurement of an amount of oxygen present in the calibration gas makes it possible to determine a drift of the measurement of said measuring member relative to the actual known amount of oxygen present in the calibration gas, the device comprises a microcontroller in communication with the measuring member to perform an automatic calibration of the measuring member based on the determined drift, the at least one member for measuring the amount of oxygen comprises a zirconium probe able to measure the partial pressure of oxygen present in a gas, wherein the device comprises a temperature sensor arranged at the zirconium probe and connected to the microcontroller, such that the microcontroller is able to vary a supply voltage of the zirconium probe based on the measured temperature.

2. The measuring device according to claim 1, wherein the device comprises a selection module controlled by the microcontroller and able to place, as selected, the first inlet or second inlet in communication with the measuring member to analyze either the gas coming from the first inlet, or the calibration gas coming from the second inlet.

3. The measuring device according to claim 2, wherein the selection module is a pneumatic selection module.

4. The measuring device according to claim 3, wherein the pneumatic selection module comprises a solenoid valve comprising two inlets, respectively connected to the first inlet and second inlet of the measuring device, and an outlet in communication with the measuring member.

5. The measuring device according to claim 1, wherein the device comprises a pressure sensor arranged at the zirconium probe and connected to the microcontroller.

6. An air separation module to generate inerting gas in a system for inerting at least one fuel tank of an aircraft, the module inwardly has at least one permeable membrane, and comprises an inlet for compressed air intended to pass through the membrane, an outlet for air enriched with oxygen, and an outlet for oxygen-depleted air called inerting gas, wherein the device comprises a measuring device according to claim 1, the first inlet of the measuring device is connected to the outlet for oxygen-depleted air of the air separation module, and the second inlet of the measuring device is connected or intended to be connected to a calibration gas source.

* * * * *